United States Patent
Brodnick et al.

(10) Patent No.: US 10,489,911 B2
(45) Date of Patent: Nov. 26, 2019

(54) DETERMINING RESPIRATORY PHASE FROM FLUOROSCOPIC IMAGES

(71) Applicant: APN Health, LLC, Pewaukee, WI (US)

(72) Inventors: Donald Brodnick, Cedarburg, WI (US); Shivani Kohut, Fayetteville, NC (US)

(73) Assignee: APN Health, LLC, Pewaukee, WI (US)

( * ) Notice: Subject to any disclaimer, the term of this patent is extended or adjusted under 35 U.S.C. 154(b) by 16 days.

(21) Appl. No.: 15/891,669

(22) Filed: Feb. 8, 2018

(65) Prior Publication Data
US 2019/0244355 A1    Aug. 8, 2019

(51) Int. Cl.
*G06T 7/00* (2017.01)
*A61B 6/00* (2006.01)
*G06T 5/20* (2006.01)
*G06T 5/00* (2006.01)

(52) U.S. Cl.
CPC .......... *G06T 7/0016* (2013.01); *A61B 6/485* (2013.01); *A61B 6/50* (2013.01); *G06T 5/002* (2013.01); *G06T 5/20* (2013.01); *G06T 2207/10064* (2013.01); *G06T 2207/20021* (2013.01)

(58) Field of Classification Search
CPC .......... A61B 6/12; A61B 6/504; G06T 5/001; G06T 2207/10068
USPC ....... 382/128, 130, 131, 132, 170, 209, 278, 382/282, 307; 128/922, 923
See application file for complete search history.

(56) References Cited

U.S. PATENT DOCUMENTS

| | | | | |
|---|---|---|---|---|
| 6,377,046 B1 * | 4/2002 | Debbins | ................ | G01R 33/54 324/309 |
| 6,466,017 B1 * | 10/2002 | Ganin | ................ | G01R 33/482 324/307 |
| 6,771,998 B2 * | 8/2004 | Kirsch | ............ | G01R 33/56509 324/307 |
| 6,937,696 B1 * | 8/2005 | Mostafavi | .............. | A61B 5/113 378/65 |

(Continued)

*Primary Examiner* — Yosef Kassa
(74) *Attorney, Agent, or Firm* — Jansson Munger McKinley & Kirby Ltd.

(57) ABSTRACT

A method of determining respiratory phase of a living body from a sequence of digitized fluoroscopic images of a living-body region exhibiting respiratory displacement. The method employs programmable computing apparatus and includes the steps of: (1) in each living-body-region image in the sequence, defining one or more zones with each image having identical image-to-image zone locations, sizes, and shapes; (2) for each image, computing an average pixel intensity for each zone to form a sequence thereof for each zone; (3) for each zone, modifying the average pixel intensities by (a) computing the mean value of the sequence of average pixel intensities for such zone, (b) subtracting the mean from each average pixel intensity in the zone, and (c) summing the absolute values of the modified average pixel intensities to form a zone-sequence sum A; (4) for each zone, computing absolute-value first differences for each sequential pair of average pixel intensities and summing the differences to form a zone-sequence first-difference sum B; (5) selecting the zone having the highest ratio A/B; and (6) using the sequence of modified average pixel intensities of the selected zone to determine respiratory phase.

12 Claims, 11 Drawing Sheets

(56) References Cited

U.S. PATENT DOCUMENTS

| | | | | |
|---|---|---|---|---|
| 7,668,585 B2* | 2/2010 | Green | .................... | A61B 5/113 |
| | | | | 378/8 |
| 7,697,972 B2* | 4/2010 | Verard | ............... | A61B 1/00071 |
| | | | | 600/407 |
| 7,720,196 B2* | 5/2010 | Zhang | .................... | A61B 5/113 |
| | | | | 378/65 |
| 7,725,163 B2* | 5/2010 | Schmitz | ............... | A61B 6/4233 |
| | | | | 378/65 |
| 8,483,801 B2* | 7/2013 | Edwards | ............. | A61B 5/7289 |
| | | | | 600/414 |
| 8,696,549 B2* | 4/2014 | Holsing | ............... | A61B 1/2676 |
| | | | | 600/117 |

\* cited by examiner

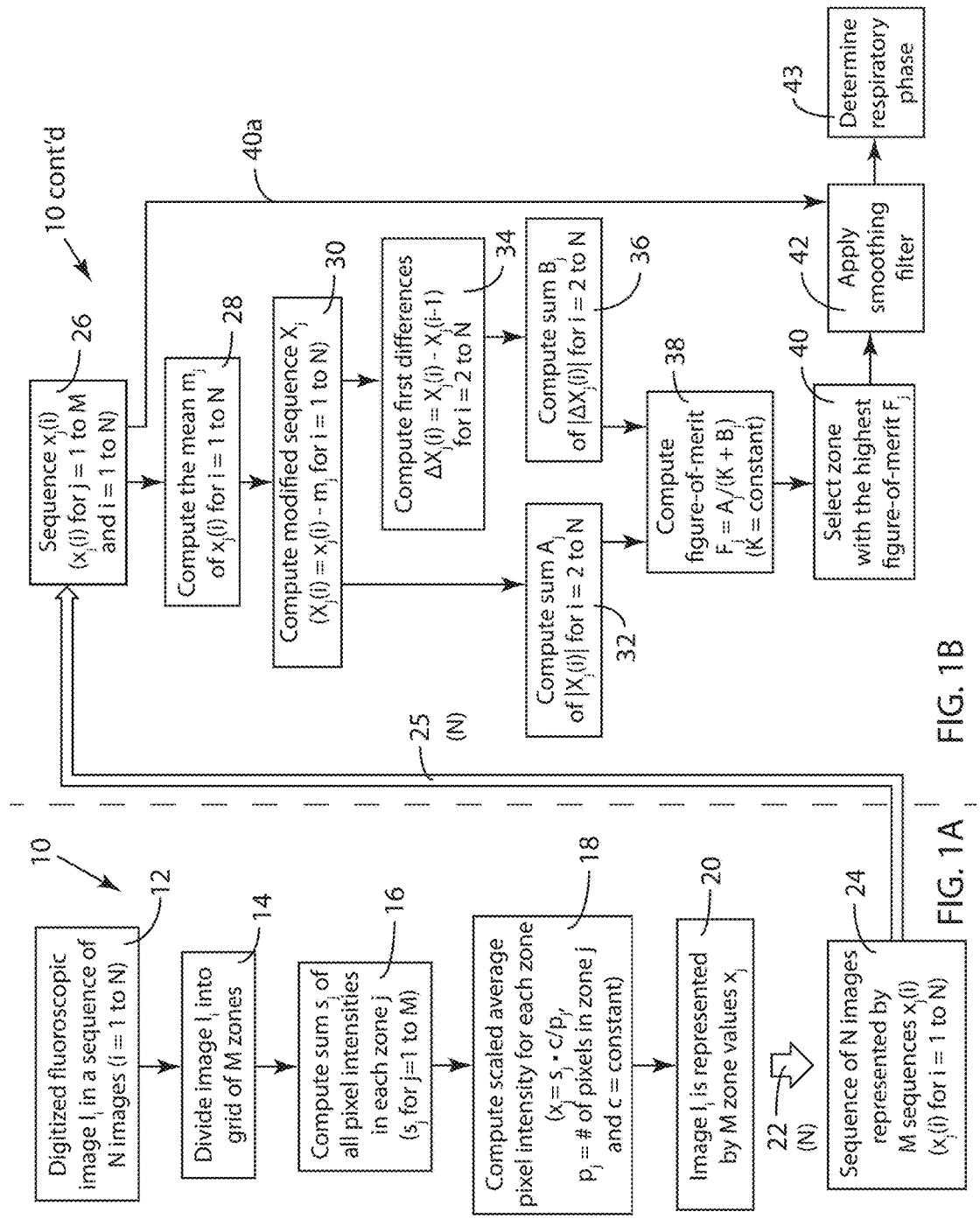

DETERMINING RESPIRATORY PHASE FROM FLUOROSCOPIC IMAGES

FIELD OF THE INVENTION

This invention is related generally to the field of medical fluoroscopy and more particularly to technology for synchronizing processes and signals with the respiration cycle of a living body.

BACKGROUND OF THE INVENTION

There is a need during some medical procedures, such as in electrophysiology studies, to process images and cardiac electrical signals in synchronization with the respiration of a patient or to selectively base certain processes on the instantaneous phase of the respiration cycle. In electrophysiology, for example, the important issue is the motion of the heart and catheters within the heart which result from respiration and not the actual perfusion of air into the lungs. In such cases, the motion of the diaphragm or lungs or other respiration-driven movement may be of more interest than actual oxygenation of blood, and so estimation of respiratory phase is more particularly directed at tracking the motion of the diaphragm which may occur during respiration or during obstructed apnea or even perhaps during artificial ventilation.

Other methods exist in the art for estimating respiratory phase from fluoroscopic images. For example, U.S. patent application Ser. No. 15/487,245 titled "Rapid 3D Cardiac Parameter Mapping" (Sra et al.), filed on Apr. 13, 2017, discloses a method which estimates respiratory phase by analyzing the motion of an identified cardiac sensor, such as a catheter, placed in the heart. Such method determines the respiratory phase of an image from changes from frame-to-frame in a single coordinate of the positions of the identified sensor.

There is a need for a method which takes advantage of the larger amount of data in an image which contains some information about respiratory phase. When portions of a fluoroscopic image larger than individual objects such as a catheter include anatomic structures such as the diaphragm, ribs or lung which undergo displacement within the image due to respiration, such portions of the image can provide a more reliable indication of respiratory phase than the local motion of an object such as a catheter.

OBJECTS OF THE INVENTION

It is an object of the inventive method of determining respiratory phase of a living body from a sequence of digitized fluoroscopic images of a living-body region exhibiting respiratory displacement to provide an estimate of respiratory phase without the need for a dedicated sensor.

Another object of this inventive method is to determine respiratory phase in a rapid manner such that synchronization of the processing of images and other data such as cardiac electrical signals with respiration can be done rapidly enough to be useful during a medical procedure.

Yet another object of this invention is to provide a method of determining respiratory phase which selects which region of a fluoroscopic image sequence is the best region for such determination.

It is a further object of the present invention to provide a method for determining respiratory phase which will provide a reliable estimate under a wide range of respiratory motion profiles.

Another object of this inventive method is to provide estimates of respiratory phase from which predictions (extrapolated estimates) of respiratory phase may be useful, thereby lowering the total X-ray exposure to a patient during a procedure.

Yet another object of this invention is to provide a method which reduces the effect of X-ray image noise on the estimate of respiratory phase.

These and other objects of the invention will be apparent from the following descriptions and from the drawings.

SUMMARY OF THE INVENTION

The present invention is a method of determining respiratory phase of a living body from a sequence of digitized fluoroscopic images of a living-body region exhibiting respiratory displacement. The method employs programmable computing apparatus and includes the steps of: (1) in each living-body-region image in the sequence, defining one or more zones with each image having identical image-to-image zone locations, sizes, and shapes; (2) for each image, computing an average pixel intensity for each zone to form a sequence thereof for each zone; (3) for each zone, modifying the average pixel intensities by (a) computing the mean value of the sequence of average pixel intensities for such zone, (b) subtracting the mean from each average pixel intensity in the zone, and (c) summing the absolute values of the modified average pixel intensities to form a zone-sequence sum A; (4) for each zone, computing absolute-value first differences for each sequential pair of average pixel intensities and summing the differences to form a zone-sequence first-difference sum B; (5) selecting the zone having the highest ratio A/B; and (6) using the sequence of modified average pixel intensities of the selected zone to determine respiratory phase.

In preferred embodiments, the method further includes applying a smoothing filter to the sequence of average pixel intensities for the selected zone. In some of these embodiments, the smoothing filter is a moving-average filter. In some such embodiments, the moving-average filter may be a one-second moving-average filter, and in others, the moving-average filter may depend on a measured cardiac rate of the living body.

In some preferred embodiments of the inventive method of determining respiratory phase, the one or more zones completely cover each image.

In some preferred embodiments, the sizes of all the zones within an image are identical, and in some preferred embodiments, the shapes of all the zones in an image are identical.

In some preferred embodiments, the forming for each zone of its sequence of average pixel intensities includes applying a scale factor to the average pixel intensities and using the same scale factor for each zone.

In some highly-preferred embodiments, the forming for each zone of its zone-sequence first-difference sum B further includes the addition of a constant to the zone-sequence first-difference sum B.

In other embodiments, the inventive method of determining respiratory phase further includes the steps of extrapolating respiratory phase estimates forward in time beyond a most recent phase determination and gating the generation or capture of the sequence of digitized fluoroscopic images of a living-body region based on the extrapolated phase estimates.

In highly-preferred embodiments of the method of determining respiratory phase, the zones are non-overlapping zones.

The term "sizes" as used herein in describing zones within a fluoroscopic image refers only to the amount of area covered by a zone.

BRIEF DESCRIPTION OF THE DRAWINGS

FIGS. 1A and 1B together constitute a schematic flowchart of an embodiment of the inventive method of determining respiratory phase of a living body from a sequence of digitized fluoroscopic images of a living-body region exhibiting respiratory displacement. FIG. 1A is a schematic flowchart of method steps which operate on each digitized image in the sequence of images, transforming the image sequence into a set of sequences of scaled average pixel intensity values. Each such numerical sequence is associated with a zone of the fluoroscopic images.

FIG. 1B is a schematic flowchart of method steps which operate on each of the numerical sequences to compute figures-of-merit for each such sequence and to select the best zone from which to determine respiratory phase.

FIG. 4 is a plot of the sequence of average pixel intensities for the zone selected by the method embodiment of FIGS. 1A and 1B, based on the selected zone having the highest figure-of-merit in the example sequence of fluoroscopic images from which the images of FIGS. 2A and 3A were taken.

FIG. 5 is a plot of the sequence of average pixel intensities for another representative zone in the example, such zone having the next-to-highest figure-of-merit.

FIG. 6 is a plot of the sequence of average pixel intensities for a third representative zone in the example, such zone having the lowest figure-of-merit.

FIG. 7 is a plot of the sequence of average pixel intensities for a fourth representative zone in the example, such zone having the next-to-lowest figure-of-merit.

In FIG. 8, this sequence has been smoothed by a moving-window averaging filter having a one-second moving window.

In FIG. 9, this sequence has been smoothed by a moving-window averaging filter having a moving window 0.733 seconds long.

DETAILED DESCRIPTION OF PREFERRED EMBODIMENTS

FIGS. 1A and 1B are schematic flowcharts (block diagrams) of an embodiment 10 of the inventive method of determining respiratory phase of a living body from a sequence of digitized fluoroscopic images of a living-body region exhibiting respiratory displacement. The flowchart of FIG. 1A illustrates method steps which operate on each digitized image in the sequence of images, transforming the image sequence into a set of numerical sequences of scaled average pixel intensity values. Each numerical sequence is associated with a zone of the fluoroscopic images.

The flowchart of FIG. 1B illustrates method steps which operate on each of the numerical sequences generated in the steps of FIG. 1A to compute figures-of-merit for each such numerical sequence (each zone) and to select the best zone from which to determine respiratory phase.

A sequence of fluoroscopic images is a series of images taken rapidly, typically at a prescribed frame rate. Typical frame rates may be 7.5 or 15 frames per second (fps) but other frame rates may be used depending on the needs of the procedure being performed. The example presented in this document uses data captured at 15 fps; such a frame rate is not intended to be limiting; other frame rates are within the scope of this invention.

Figure 2B:
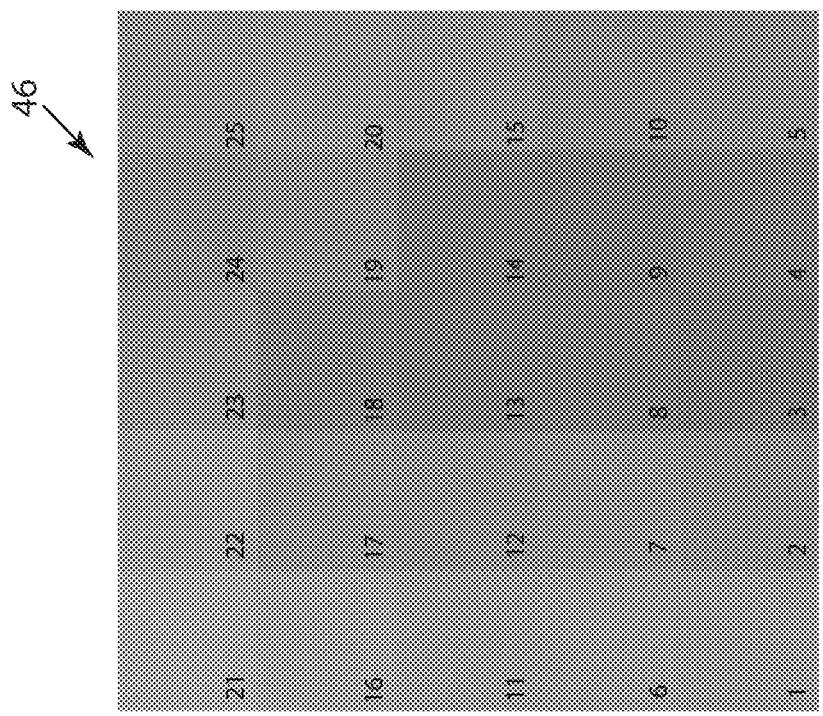
FIG. 2B is a visual illustration of the results of averaging the pixel intensities within each of the 25 zones in the representative frame of FIG. 2A.

The exemplary fluoroscopic images in the example are images having 1,000×1,000 pixels (picture elements). Twenty-five (25) equally-sized square zones are defined in the exemplary images so that each zone is a 200×200 pixel zone. The image resolution and zone configurations of the exemplary images are not intended to be limiting; other image resolutions and zone configurations are within the scope of this invention. In the example, the zone numbering has arbitrarily been chosen as illustrated in FIGS. 2B and 3B.

In the exemplary images, each pixel has a pixel intensity represented by 8 bits such that a totally black pixel has a pixel intensity of 0 and a totally white pixel has a pixel intensity of 255. Such bit resolution or color assignment are again not intended to be limiting.

The method steps of FIGS. 1A and 1B are carried out in automatic computer apparatus. The number of computations in the inventive method and the rate at which such computations must be carried out in order for the method to be useful require that high-speed computational equipment such as programmable computing apparatus must be employed. Such apparatus may include one or more general-purpose computers and/or FPGA devices (field-programmable gate arrays) programmed to carry out the necessary computations and logic of the inventive method. The term "programmable" as used herein is also intended to include fully-custom circuitry designed (programmed) to carry out the computations and logic such that software or firmware are not required as part of such apparatus.

In the flowcharts of FIGS. 1A and 1B, the individual blocks representing the method steps may be referred to herein as method elements.

Referring now to FIG. 1A, method element 12 represents a single digitized fluoroscopic image $I_i$ in a sequence of N images. In the example presented below, the images are as described above, and there are N=148 images in the exemplary sequence. In method step 14, M zones are defined within image $I_i$ such that image $I_i$ is divided into M zones.

In the example, there are M=25 equally-sized square zones which form a grid as described above and shown in FIGS. 2B and 3B.

In method element 16, a sum $s_j$ of all of the pixel intensities in each of the M zones ($s_j$ for j=1 to M) is computed. In method element 18, a scaled average pixel intensity $x_j$ is computed for each zone j as $x_j=s_j \cdot c/p_j$ where $p_j$ is the number of pixels in zone j and c is a scaling constant. Note that if no scaling is employed (c=1), the average pixel intensity is the sum $s_j$ divided by the number of pixels $p_j$ in zone j. In the example of this application, there are 40,000 pixels in each zone.

However, scaling may be employed in order to take advantage of some of the extra precision which comes about from using integer arithmetic for the purpose of more rapid computations. In the example presented below, instead of dividing each sum $s_j$ by 40,000, each sum $s_j$ is divided by 8,192 which is rapidly carried out by a simple bit-shifting step since 8,192 is $2^{13}$. In other words, the constant c in the example is c=40,000/8,192=4.8828; each value of average pixel intensity is scaled by a factor of 4.8828. Note that the ordinate of each of the plots in FIGS. 4-9 is scaled in this fashion; thus, average pixel intensity values are well above 255.

Method element 20 simply shows that each image $I_i$ at this stage in method embodiment 10 is represented by a set of M zone values $x_j$ (scaled average pixel intensities), and arrow 22 indicates that since there are N fluoroscopic images in the image sequence, there are M sequences $x_j(i)$ of such N zone values, illustrated by method element 24.

Arrow 25 connects the single-image zone computations of method embodiment 10 in FIG. 1A with the image-sequence zone computations of FIG. 1B. The remaining method steps of method embodiment 10 are computations which lead to figures-of-merit $F_j$ of each of the M zones, evaluated across the entire sequence of N images. The steps of this portion (10 cont'd) of embodiment 10 result in the selection of the best zone from which to determine respiratory phase (or in the special case when M=1, whether or not there is adequate information in the single zone by which to make such a determination).

Referring now to FIG. 1B, method step 26 simply reiterates that in this portion of method embodiment 10, computations are being made on each of the M numerical sequences. In method step 28, mean values $m_j$ for each numerical sequence $x_j(i)$ are computed, and in method element 30, modified numerical sequences $X_j(i)$ are computed by subtracting the mean $m_j$ from each numerical value in the sequence $x_j(i)$, resulting in M modified numerical sequences $X_j(i)$, one for each image in the image sequence.

In method element 32, a sum $A_j$ of the absolute values of the modified numerical sequence $X_j(i)$ is computed, resulting in M values $A_j$, one for each zone. (In method embodiment 10, this sum is specified as being computed for i=2 to N based on later usage of the sum, but a sum from i=1 to N will also be acceptable.) In method element 34, a numerical sequence of first differences $\Delta X_j(i)$ is computed by differencing consecutive values in numerical sequence $\Delta X_j(i)=X_j(i)-X_j(i-1)$ for i=2 to N. Then in method element 36, in similar fashion to method element 32, a sum $B_j$ of the absolute values of the numerical sequence $\Delta X_j(i)$ is computed, resulting in M values $B_j$, one for each zone. (Note that since the first differences are being calculated, method element 34 could alternatively have the unmodified numerical sequence $x_j(i)$ as its input.)

In method element 38, a figure-of-merit $F_j$ is computed for each zone by computing the ratio of and $(K+B_j)$ where K is a constant. The ratio of $A_j$ to $B_j$ basically rewards zones which have the lowest dominant frequency of intensity variation over the entire image sequence. In other words, a higher dominant frequency results in a higher value of the first-difference sum $B_j$ and thus a lower figure-of-merit. The addition of the constant K in the computation of figure-of-merit $F_j$ provides a slight bias toward zones having larger numerical range within their modified numerical sequences $X_j(i)$. If a numerical sequence $X_j(i)$ is thought of as a signal, a larger numerical range within such signal can be described as a stronger signal. (It has been found that a value for K of around 4 adds a small but adequate bias toward larger signals when more than one signal have the same dominant frequency. However, such a value for K is not intended to be limiting. A zero value for K also is possible, but for practical purposes, in the unlikely event that B has a value of zero, with a non-zero value for K, a divide-by-zero occurrence is avoided.)

In method step 40, the zone having the highest figure-of-merit $F_j$ is selected as the best zone from which to determine respiratory phase. In method step 42, a smoothing filter is applied to the sequence of scaled average pixel intensities $x_j(i)$ where j is the selected zone number. Flow path 40a indicates that $x_j(i)$ is provided to the filter from method element 26. Finally, respiratory phase is determined in method element 43 from the filtered numerical sequence using techniques well-known to those skilled in signal processing and/or mathematical analysis. It may be as straightforward as identifying the point of maximum inhalation or maximum exhalation. And it is even possible using some methods to determine respiratory phase even if less than an entire respiratory cycle is found in an image sequence. For example, one possible method is to compare even a very brief sequence of average pixel intensity values during a period of increasing or decreasing values with portions of previously-obtained sequences of values as long as the fluoroscope has not been moved relative to the patient.

Figure 2A:
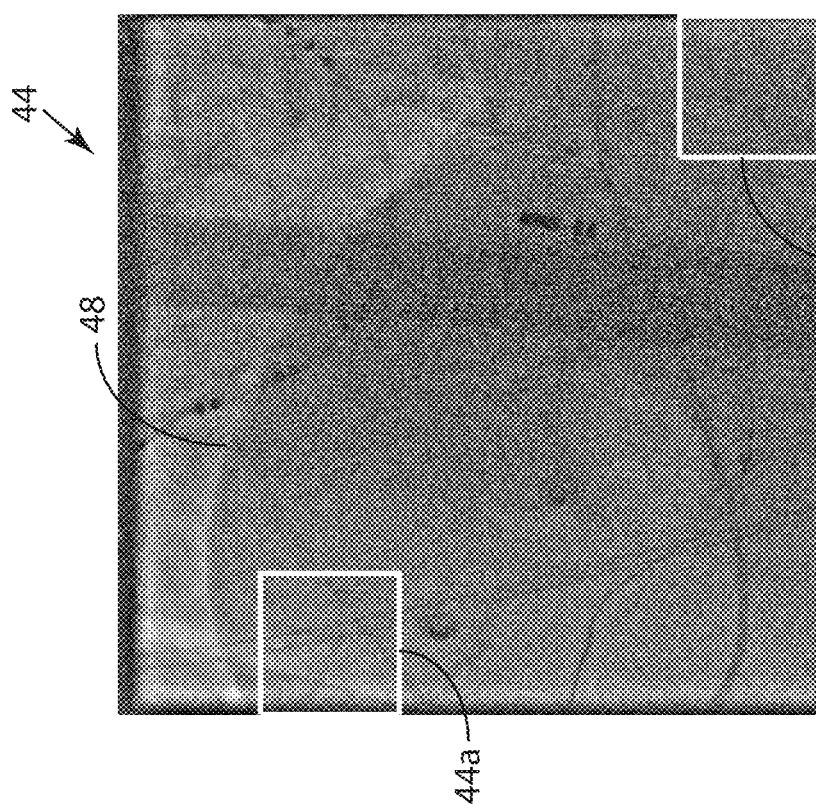
FIG. 2A is a representative frame in a sequence of fluoroscopic images. The fluoroscopic frame of FIG. 2A is taken at a time near the end of exhalation.
Figure 3A:
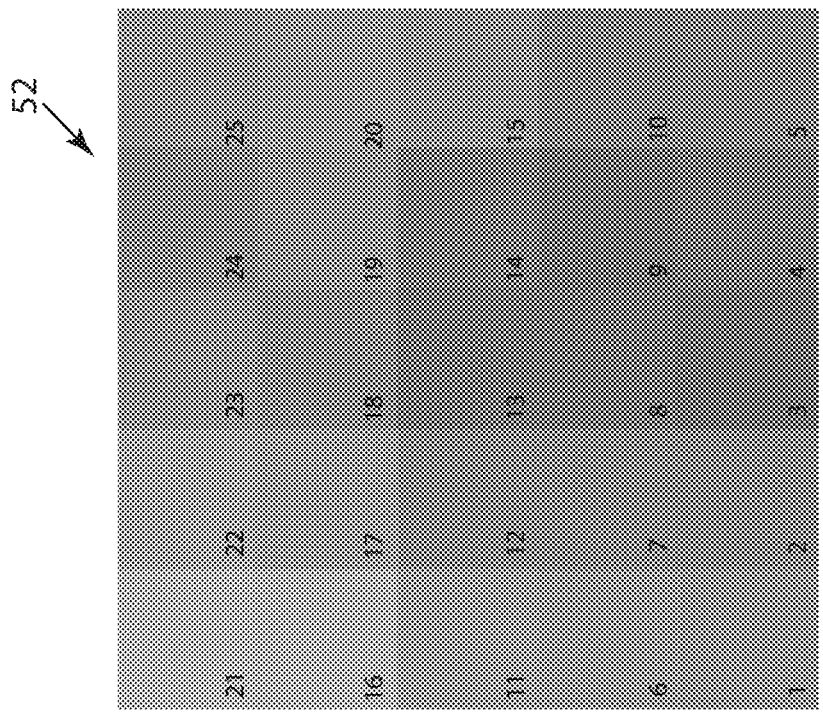
FIG. 3A is another representative frame in a sequence of fluoroscopic images. The fluoroscopic frame of FIG. 3A is taken at a time of maximum inhalation.
Figure 3B:
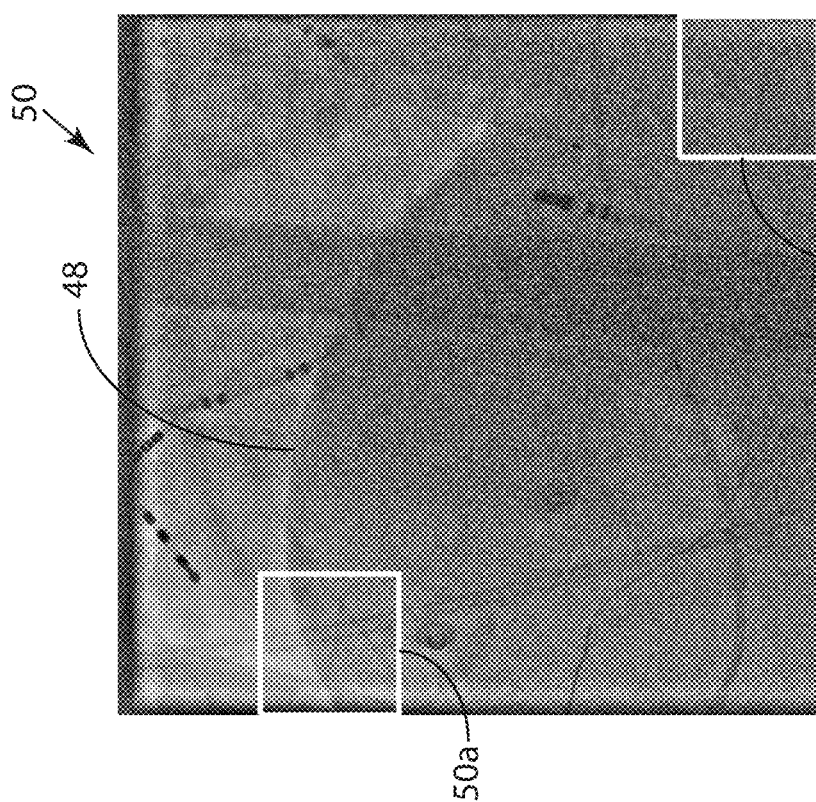
FIG. 3B is a visual illustration of the results of averaging the pixel intensities within each of the 25 zones in the representative frame of FIG. 3A.

FIGS. 2A and 3A are representative fluoroscopic images from an exemplary image sequence of 148 images as introduced above. FIG. 2A is a representative frame 44 at a time near the end of exhalation, and FIG. 3A is a representative frame 50 at a time of maximum inhalation. FIGS. 2B and 3B show depictions 46 and 52, respectively, of the twenty-five zones as defined above with the gray-level shading corresponding to the average pixel intensities as determined by the method of method embodiment 10.

FIG. 2A includes zone 16 and zone 5 marked by reference numbers 44a and 44b, respectively, and FIG. 3A includes zone 16 and zone 5 marked by reference numbers 50a and 50b, respectively. These specific frames are shown to illustrate the much larger change in average pixel intensity that occurs in zone 16 when compared to zone 5. By comparing images 44 and 50 in zone 16, it is easy to see that the motion of a patient's diaphragm 48 is significant in zone 16 while in zone 5, the changes are even difficult to recognize. This illustrates a fundamental feature of the inventive method, that anatomical regions which exhibit respiratory displacement are what are being sensed in the sequence of fluoroscopic images.

Figure 4:
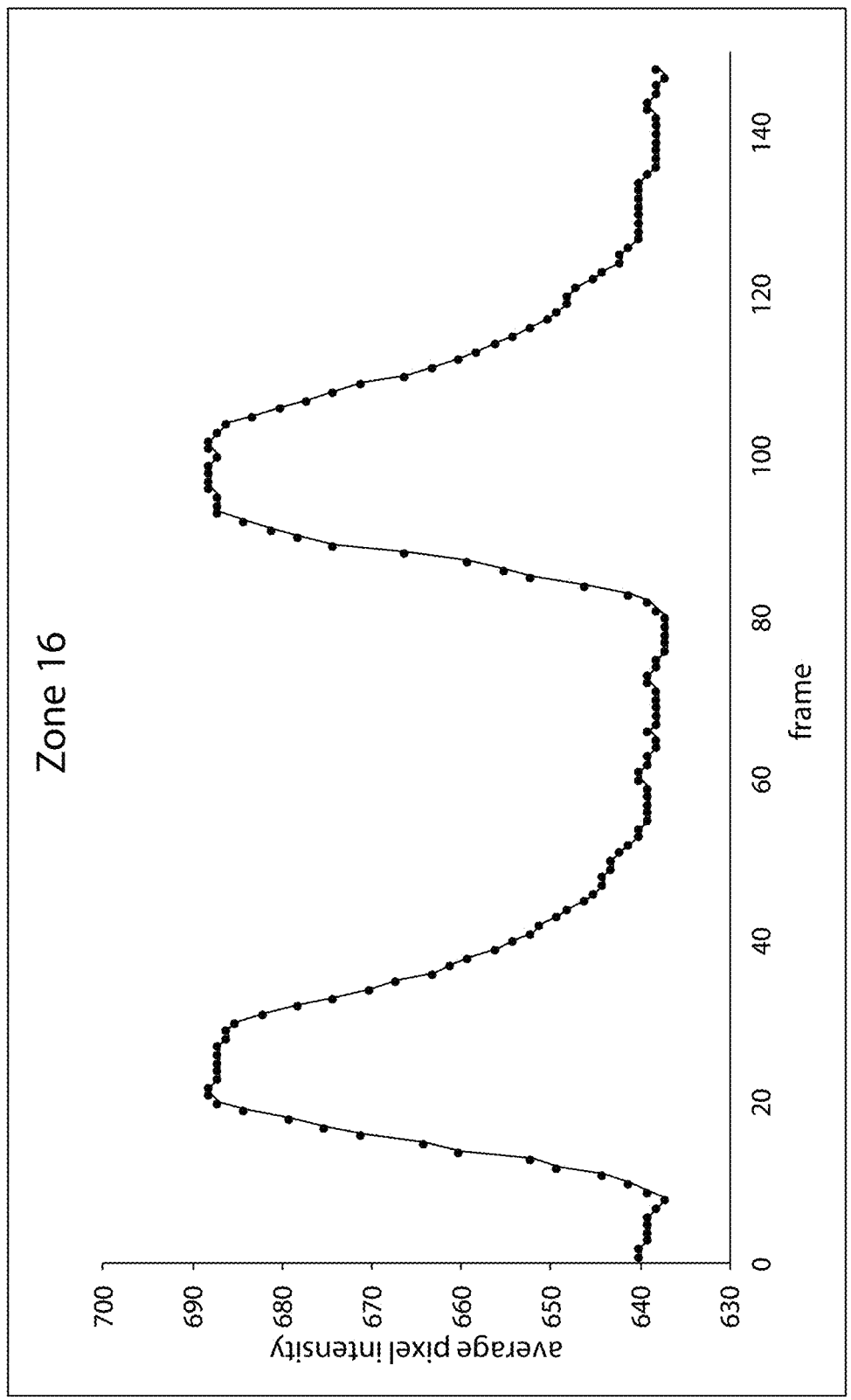
FIGS. 4 through 7 are frame-by-frame plots of sequences of average pixel intensities from four zones in the example sequence of fluoroscopic images from which the images in FIGS. 2A and 3A were taken and as computed by the method of FIG. 1A.
Figure 5:
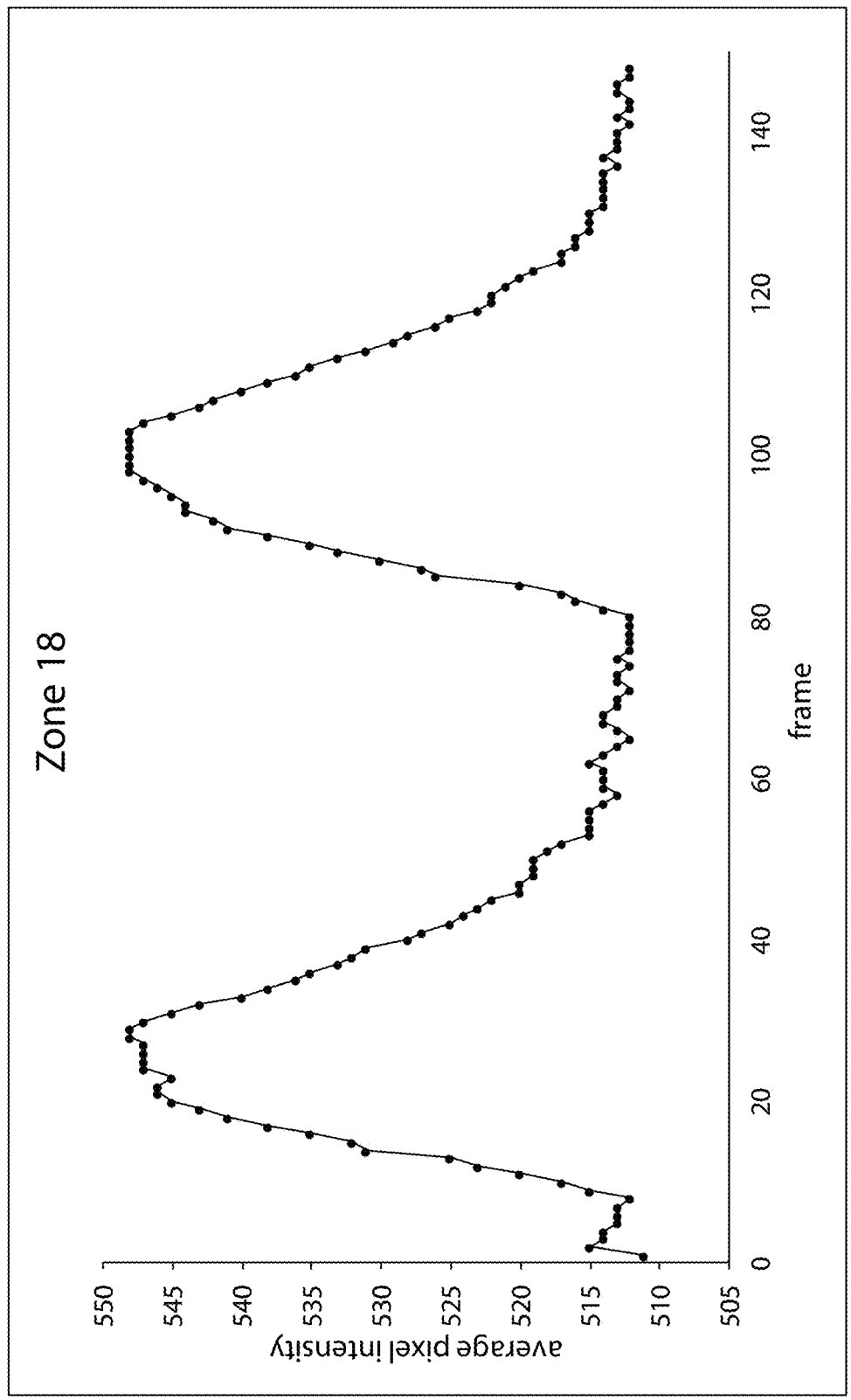
Figure 6:
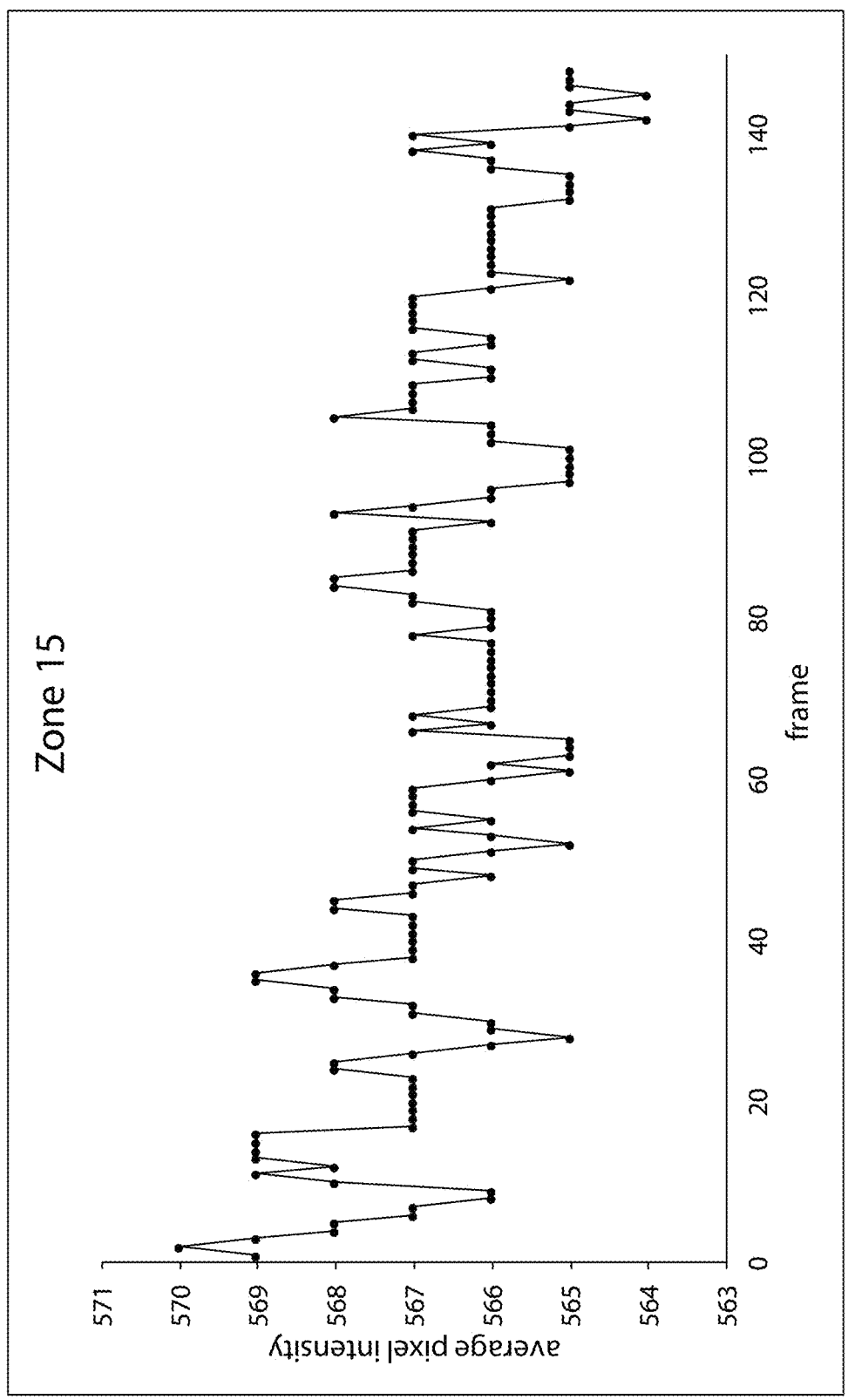
Figure 7:
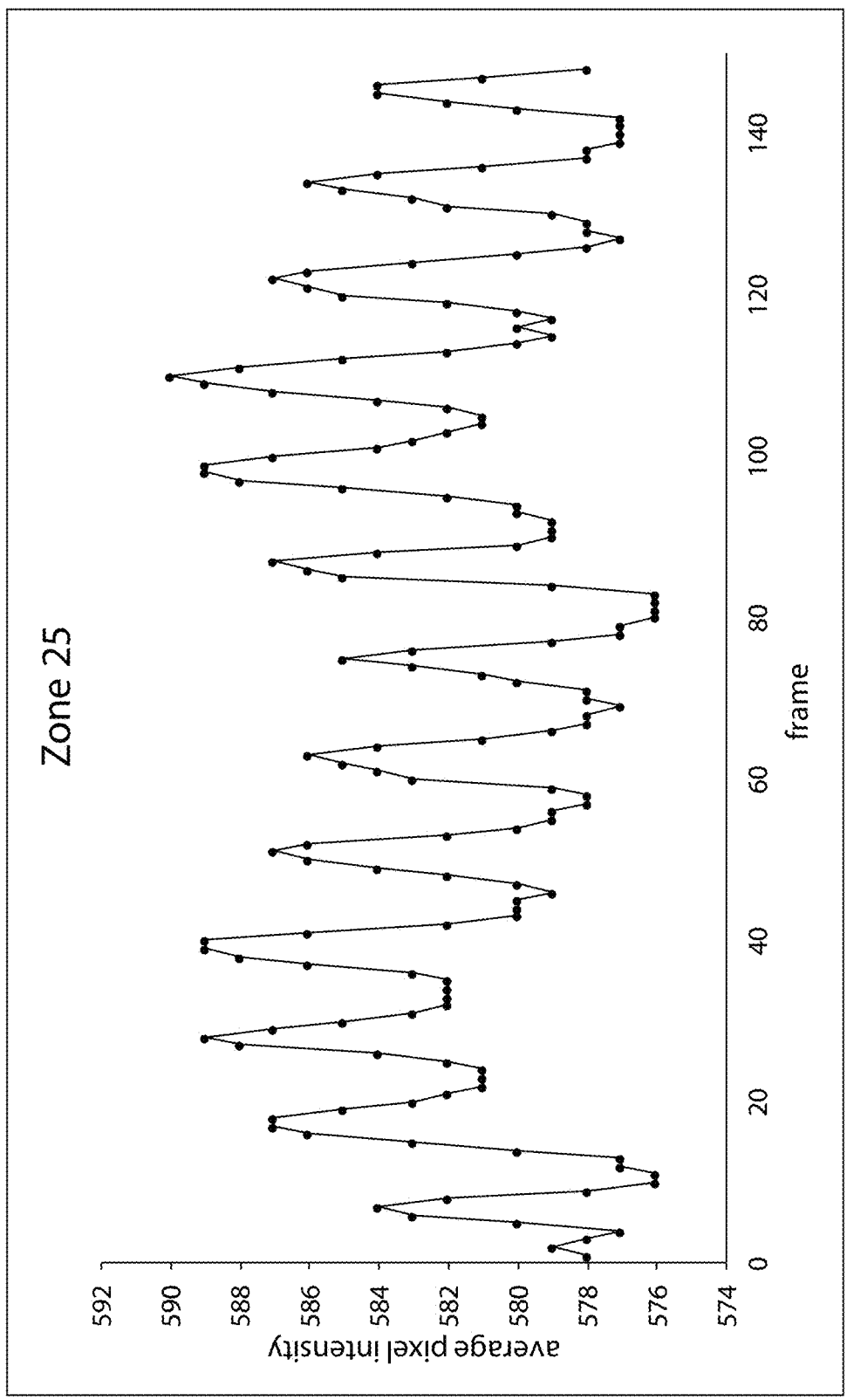

Zone 16 was found in the example to have the highest figure-of-merit ($F_{16}$=11.08) for sequence of 148 images. FIG. 4 is a frame-by-frame plot of the scaled average pixel intensity for zone 16 in the example. As points of comparison, FIG. 5 is a frame-by-frame plot of the scaled average pixel intensity for zone 18 in the example, FIG. 6 is a frame-by-frame plot of the scaled average pixel intensity for zone 15, and FIG. 7 is a frame-by-frame plot of the scaled average pixel intensity for zone 25. Zone 18 was found to have the next-to-the-highest figure-of-merit (9.83), zone 15 was found to have the lowest figure-of-merit (1.74), and zone 25 was found to have the next-to-the-lowest figure-of-merit (1.95). (Note that in making comparisons among the plots of FIGS. 4-7, one should also take into account the range of values along which the scaled average pixel intensities vary.)

Figure 8:
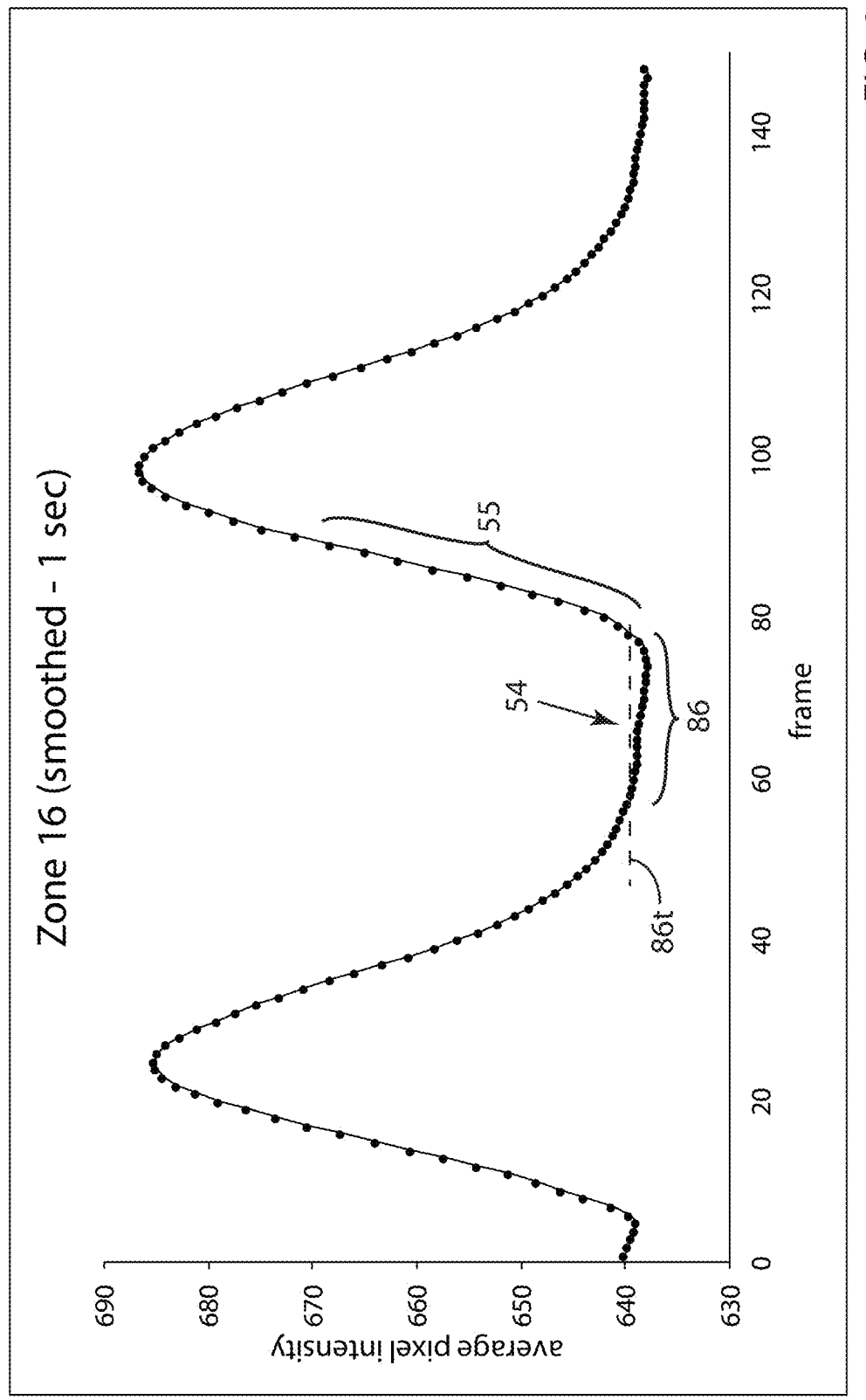
FIG. 8 is a plot of the sequence of FIG. 4, such sequence being the selected zone.
Figure 9:
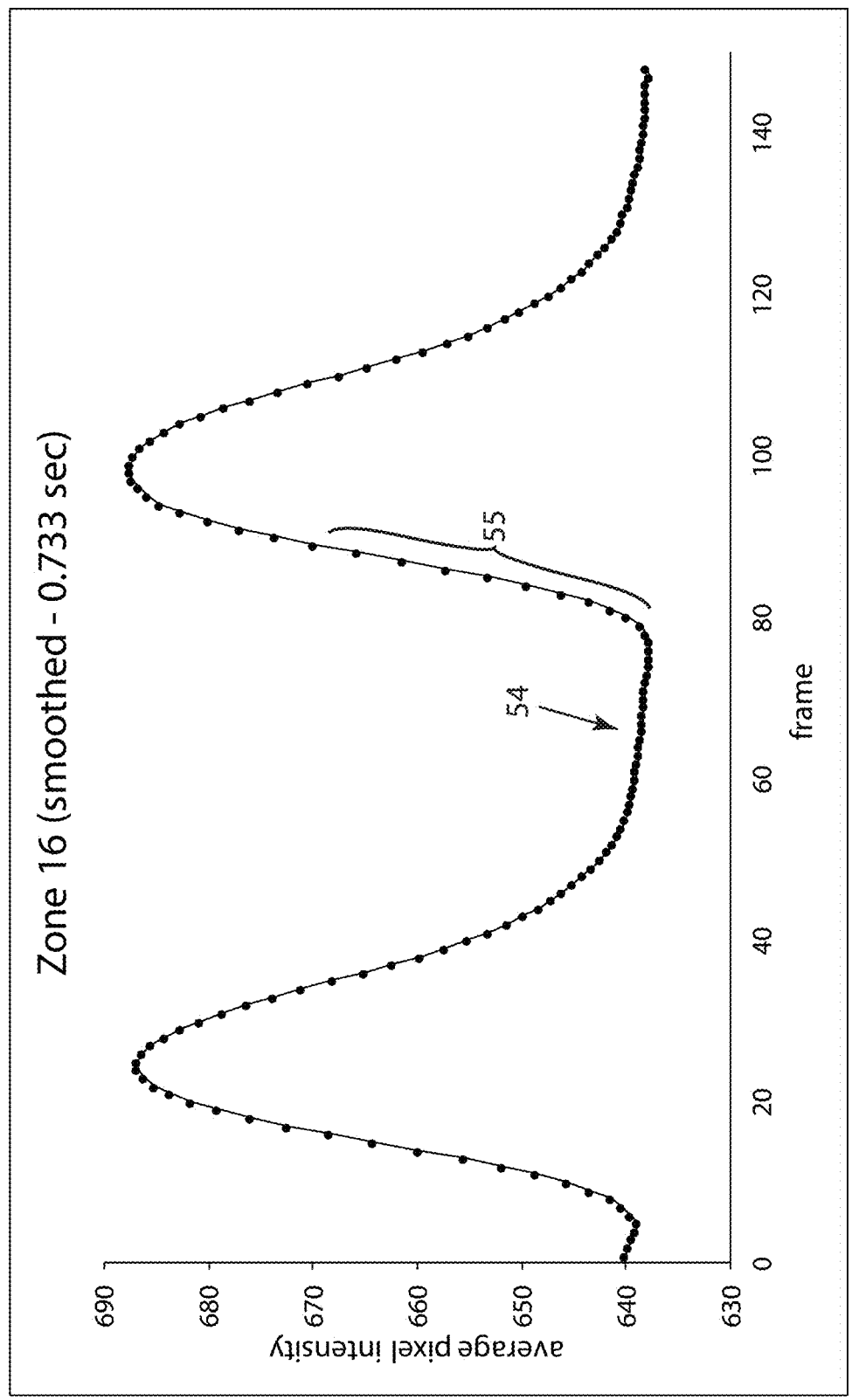
FIG. 9 is a plot of the sequence of FIG. 4, such sequence being the selected zone.

FIG. 8 is a frame-by-frame plot of the scaled average pixel intensity of FIG. 5 to which a one-second moving-window averaging filter has been applied. Moving-window averaging is well-known to those skilled in signal processing and need not be described in detail herein. FIG. 9 is a frame-by-frame plot of the scaled average pixel intensity of FIG. 5 to which a moving-window averaging filter having a moving window 0.733 seconds long (11 frames) has been applied. The 0.733 second moving-window was determined from a measurement of the cardiac cycle within the 148-image sequence. By comparing regions 54 in FIGS. 8 and 9, one can see slightly more effective filtering of the cardiac motion from the signal. As is well-known, smoothing becomes more important in the presence of more image noise, and in the case of determining the moving-window size from the cardiac cycle, the purpose of such filtering is to remove the cardiac cycle, not X-ray noise, from the scaled average pixel intensity signal as much as possible without corrupting the respiratory phase determination. One advantage of removing the cardiac cycle can be seen in the comparison between FIGS. 8 and 9 by observing the steeper leading edge 55 of the respiratory cycle which is evident in FIG. 9.

While the example presented herein includes a very useful definition of zones within images, it is noted that within the scope of the present inventive method, (1) fluoroscopic images need not be square, (2) zones need not be square or rectangular, (3) zones need not have identical sizes (areas), (4) zones need not have identical shapes, and (5) zones need not completely cover the area of the image. The key parameters within the inventive method relate to the average pixel intensities within zones, and zone definitions which provide good assessments of average pixel intensities of the zones are all that is required. FIGS. 10A-10F are schematic illustrations of some variations of zone definitions within fluoroscopic images which may be processed by the inventive method, and the variations illustrated therein are not intended to be limiting. Each of the exemplary illustrations in FIGS. 10A-10F include zones which are non-overlapping. Any regions of two or more zones which overlap cause possible lowering of the differences between the values of the figures-of-merit for the overlapping zones.

Figure 10A:
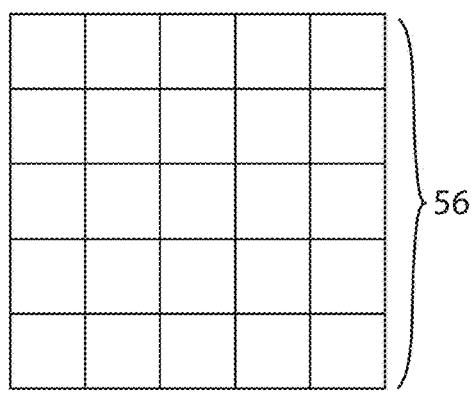
FIGS. 10A-10F are schematic illustrations of variations of zone definitions within fluoroscopic images processed by the inventive method.

FIG. 10A illustrates the simple zone definition 56 of the example described in detail above—twenty-five square zones completely covering the image area. FIGS. 10C and 10E illustrate two more zone definitions which completely cover the image area. FIG. 10C illustrates a zone definition 60 in which the zones all have identical sizes (areas) and shapes (rectangular), and FIG. 10E illustrates a zone definition 64 in which both the sizes (areas) and shapes of the zones differ.

Figure 10B:
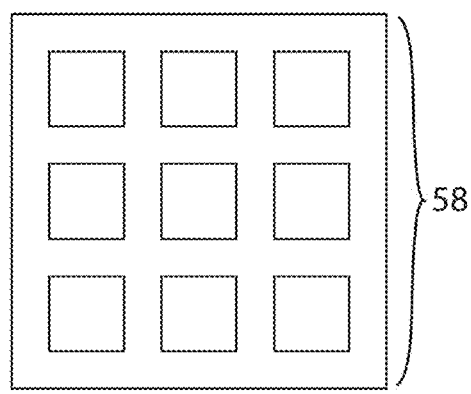
Figure 10C:
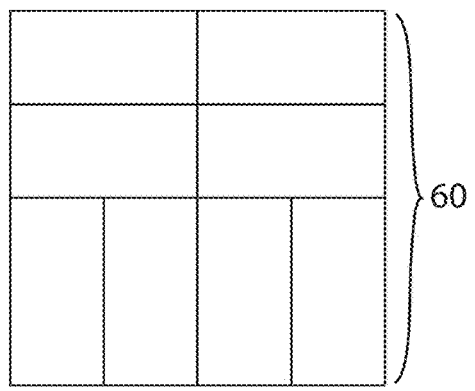
Figure 10D:
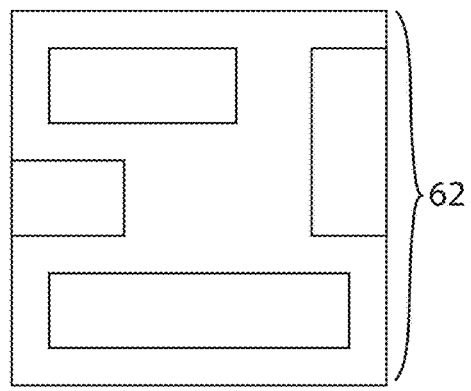
Figure 10E:
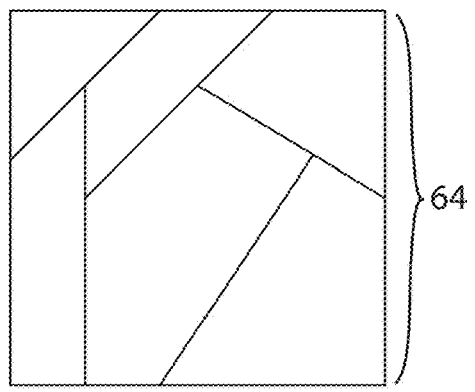
Figure 10F:
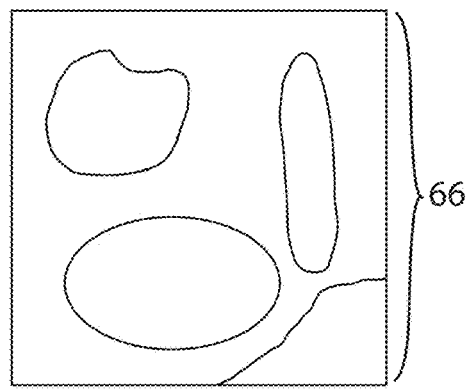

FIGS. 10B, 10D and 10F illustrate zone definitions which do not completely cover the image area. Zone definition 58 of FIG. 10B includes nine identical square zones; zone definition 62 of FIG. 10D includes four rectangular zones which have different sizes (areas) and shapes (aspect ratios); and zone definition 66 of FIG. 10F includes four irregularly-shaped zones having different sizes (areas). One example of a situation in which only partial coverage of an image may be helpful is when a fluoroscopic system places text in an image (usually near an edge of the image) that changes image-to-image.

Note that the zone definition of any of the zone definitions which do not completely cover the image area could be modified by also defining the remaining image area as an additional zone.

Of course, from a practical point-of-view, the ease and speed with which the attendant computations can be carried out are also important considerations in the step of defining zones within an image. Many of the exemplary options for zone definitions set forth in FIGS. 10A-10F will likely not satisfy such practical considerations.

Figure 11:
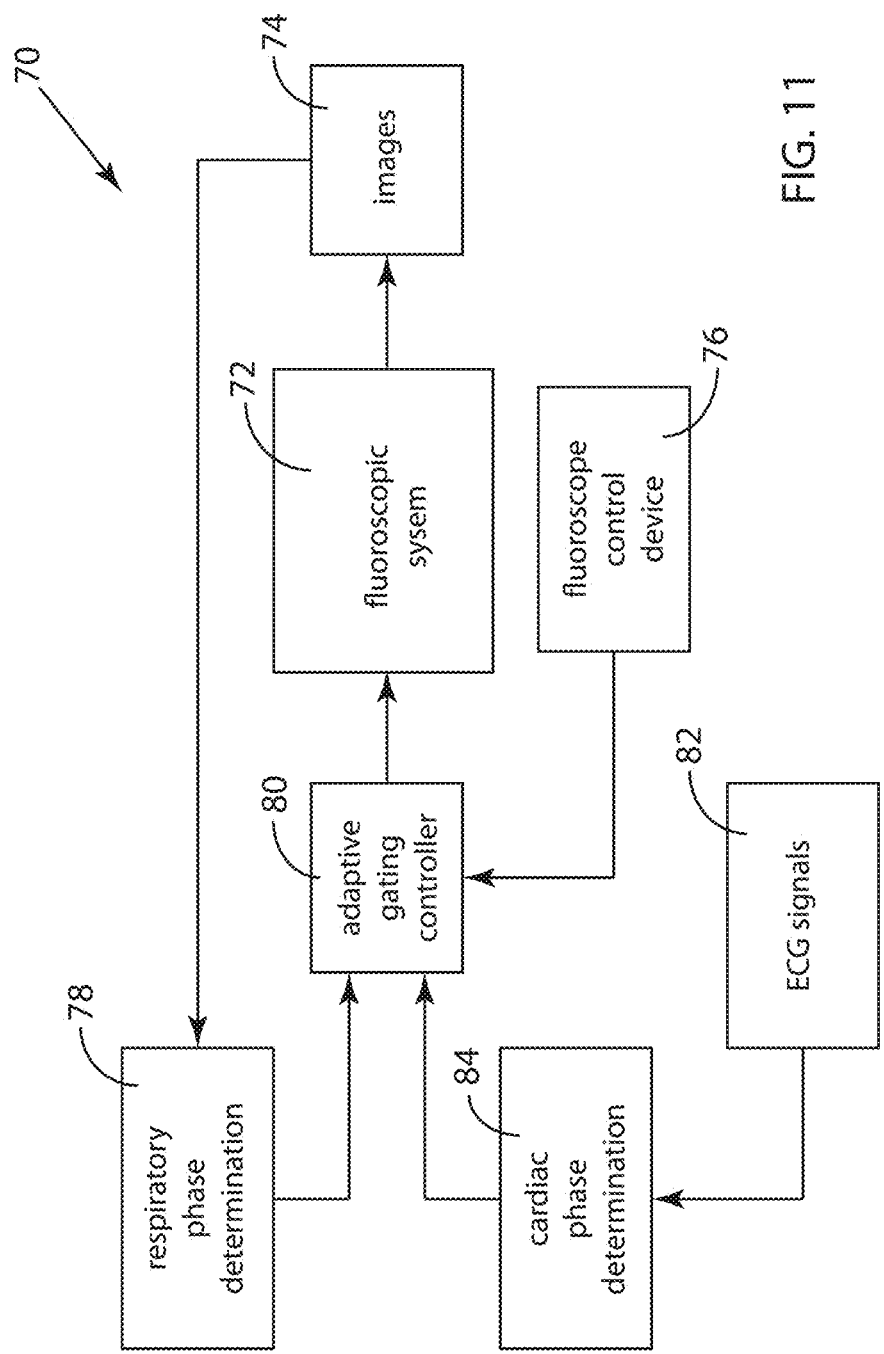
FIG. 11 is a schematic flowchart of a system which combines the inventive method of respiratory phase determination of FIGS. 1A and 1B with method steps which control the activation of a fluoroscopic system based on respiratory phase and cardiac phase.

FIG. 11 is a schematic flowchart of an embodiment 70 of an inventive method which combines an embodiment of the inventive method of respiratory phase determination (such as embodiment 10 of FIGS. 1A and 1B) with method steps which control the activation of a fluoroscopic system 72 based on respiratory phase and cardiac phase. Fluoroscopic system 72 is controlled by an adaptive gating controller 80 which is controlled by a fluoroscope control device 76. Fluoroscope control device 76 may be a pedal 76 or a foot switch 76 or other convenient switching device such as a voice recognition module 76. Most typically, fluoroscope control device 76 is a pedal; thus for convenience and simplicity, hereinafter in this description of FIG. 11, fluoroscope control device 76 will be referred to as pedal 76. The use of term pedal 76 in this fashion is not intended to be limiting; many other switching devices are contemplated as being within the scope of this invention.

Pedal 76 is an ON/OFF switching device which sends an ON/OFF signal to controller 80 to indicate that pedal 76 is either pressed (ON) or not pressed (OFF). While pedal 76 is sending an ON signal to controller 80, controller 80, using respiratory phase information from method element 78 (from method steps such as in exemplary embodiment 10 illustrated in FIGS. 1A and 1B), compares a target respiratory phase region 86 (see FIG. 8) and an estimate of current respiratory phase to determine whether or not to send an ON or OFF signal to fluoroscopic system 72 which will either start or stop the stream of fluoroscopic images being generated. Thus, when pedal 76 is in an ON position, controller 80 may either delay the start of the generation of fluoroscopic images or advance the stopping of image generation, relative to the signal being sent by pedal 76.

Referring again to FIG. 8, target respiratory phase region 86 may be defined by respiratory phases below a phase threshold 86t as indicated by a dotted line 86t. Target respiratory phase region 86 includes times (frames) along the respiratory timeline as represented by the smoothed average pixel intensity curve of FIG. 8 during which the estimated respiratory phase is below phase threshold 86t.

FIG. 11 also includes a method element 84 which represents a determination of cardiac phase derived from a set of ECG signals 82. Both respiratory and cardiac phase information may be combined within controller 80 to provide an even more intelligent gating signal to fluoroscopic system 72. Cardiac phase determination method element 84 may include cardiac phase determination methods well-known to those skilled in the area of signal processing and are not described here in detail.

While the principles of this invention have been described in connection with specific embodiments, it should be understood clearly that these descriptions are made only by way of example and are not intended to limit the scope of the invention.

The invention claimed is:

1. A method of determining respiratory phase of a living body from a sequence of digitized fluoroscopic images of a living-body region exhibiting respiratory displacement, the method employing programmable computing apparatus and comprising the steps of:

in each living-body-region image in the sequence, defining one or more zones with each image having identical image-to-image zone locations, sizes, and shapes;

for each image, computing an average pixel intensity for each zone to form a sequence thereof for each zone;

for each zone, modifying the average pixel intensities by:
computing a mean value of the sequence of average pixel intensities for the zone;
subtracting the mean value from each average pixel intensity in the zone; and
summing absolute values of the modified average pixel intensities to form a zone-sequence sum A for the zone;

for each zone, computing absolute-value first differences for each consecutive pair of average pixel intensities and summing the differences to form a zone-sequence first-difference sum B;

selecting the zone having the highest ratio A/B; and using the sequence of modified average pixel intensities of the selected zone to determine respiratory phase.

2. The method of determining respiratory phase of claim 1 further including applying a smoothing filter to the sequence of average pixel intensities for the selected zone.

3. The method of determining respiratory phase of claim 2 wherein the smoothing filter is a moving-average filter.

4. The method of determining respiratory phase of claim 3 wherein the moving-average filter is a one-second moving-average filter.

5. The method of determining respiratory phase of claim 3 wherein the moving-average filter depends on a measured cardiac rate of the living body.

6. The method of determining respiratory phase of claim 1 wherein the one or more zones completely cover each image.

7. The method of determining respiratory phase of claim 1 wherein the sizes of all of the zones within an image are identical.

8. The method of determining respiratory phase of claim 1 wherein the shapes of all of the zones within an image are identical.

9. The method of determining respiratory phase of claim 1 wherein the forming for each zone of its sequence of average pixel intensities includes applying a scale factor to the average pixel intensities and using the same scale factor for each zone.

10. The method of determining respiratory phase of claim 1 wherein the forming for each zone of its zone-sequence first-difference sum B further includes the addition of a constant to the zone-sequence first-difference sum B.

11. The method of determining respiratory phase of claim 1 further including the steps of extrapolating respiratory phase estimates forward in time beyond a most recent phase determination and gating the generation or capture of the sequence of digitized fluoroscopic images of a living-body region based on the extrapolated phase estimates.

12. The method of determining respiratory phase of claim 1 wherein the zones are non-overlapping zones.

* * * * *